United States Patent
Zhang et al.

(10) Patent No.: US 10,371,597 B2
(45) Date of Patent: Aug. 6, 2019

(54) METHOD AND DEVICE FOR TESTING GEARWHEELS

(71) Applicant: Bayerische Motoren Werke Aktiengesellschaft, Munich (DE)

(72) Inventors: Huchen Zhang, Munich (DE); Anton Wildfeuer, Niederviehbach (DE); Rainer Annast, Munich (DE)

(73) Assignee: Bayerische Motoren Werke Aktiengesellschaft, Munich (DE)

( * ) Notice: Subject to any disclaimer, the term of this patent is extended or adjusted under 35 U.S.C. 154(b) by 155 days.

(21) Appl. No.: 15/681,490

(22) Filed: Aug. 21, 2017

(65) Prior Publication Data
US 2017/0356824 A1 Dec. 14, 2017

Related U.S. Application Data

(63) Continuation of application No. PCT/EP2016/050668, filed on Jan. 14, 2016.

(30) Foreign Application Priority Data

Mar. 13, 2015 (DE) .......................... 10 2015 204 554

(51) Int. Cl.
*G01M 13/02* (2019.01)
*G01M 13/021* (2019.01)
(Continued)

(52) U.S. Cl.
CPC ...... *G01M 13/021* (2013.01); *G01N 21/9515* (2013.01); *G06T 7/0004* (2013.01)

(58) Field of Classification Search
CPC .. G01M 13/021; G01M 13/028; G01M 13/02; G01M 13/025; G01M 13/026;
(Continued)

(56) References Cited

U.S. PATENT DOCUMENTS 2,256,102 A * 9/1941 Reason .............. G02B 21/0016
356/389
5,307,676 A * 5/1994 Gutman .............. G01M 13/021
269/71

(Continued)

FOREIGN PATENT DOCUMENTS

CN 1564996 A 1/2005
CN 101335833 A 12/2008
(Continued)

OTHER PUBLICATIONS

German-language Office Action issued in counterpart German Application No. 10 2015 204 554.4 dated Nov. 30, 2015 (6 pages).
(Continued)

*Primary Examiner* — Andre J Allen
(74) *Attorney, Agent, or Firm* — Crowell & Moring LLP

(57) ABSTRACT

A apparatus is provided for carrying out an optical test method for a gearwheel. The testing apparatus includes a first camera for capturing image data of a first type of tooth flanks of the gearwheel to be tested, a position sensor for determining a rotational position of the gearwheel to be tested, a control device for evaluating the rotational position determined by this position sensor and for controlling the camera on the basis of this turning position, and a first illuminating device designed for illuminating an area of the gearwheel to be tested, which area is provided for capturing the image data.

20 Claims, 3 Drawing Sheets

(51) Int. Cl.
*G06T 7/00* (2017.01)
*G01N 21/95* (2006.01)

(58) Field of Classification Search
CPC .. G01M 13/022; G01M 13/027; G01M 13/04; G01M 7/00
USPC .......................................................... 73/162
See application file for complete search history.

(56) References Cited

U.S. PATENT DOCUMENTS

| | | | |
|---|---|---|---|
| 5,373,735 | A | 12/1994 | Gutman |
| 5,610,994 | A | 3/1997 | Stadtfeld et al. |
| 6,148,098 | A | 11/2000 | Rutschke et al. |
| 9,274,026 | B1 * | 3/2016 | Cathey et al. ...... G01M 13/021 269/71 |
| 2006/0029257 | A1 | 2/2006 | Eguchi et al. |
| 2007/0058854 | A1 | 3/2007 | Caskey et al. |
| 2008/0163502 | A1 * | 7/2008 | Siraky .................... F16H 55/18 33/1 PT |
| 2009/0001268 | A1 | 1/2009 | Tadano |
| 2011/0056344 | A1 * | 3/2011 | Dick ...................... B23D 45/14 83/13 |
| 2016/0298749 | A1 * | 10/2016 | Burger .................. F16H 49/001 |
| 2018/0128596 | A1 * | 5/2018 | Mies .................... G01B 11/005 |
| 2019/0064031 | A1 * | 2/2019 | Mies .................... G01M 13/021 |

FOREIGN PATENT DOCUMENTS

| | | |
|---|---|---|
| CN | 107003207 A * | 8/2017 |
| DE | 10 2009 023 722 A1 | 12/2010 |
| JP | 9-329413 A | 12/1997 |
| JP | 2008-185549 A | 8/2008 |

OTHER PUBLICATIONS

International Search Report (PCT/ISA/210) issued in PCT Application No. PCT/EP2016/050668 dated Mar. 7, 2016 with English translation (6 pages).
German-language Written Opinion (PCT/ISA/237) issued in PCT Application No. PCT/EP2016/050668 dated Mar. 7, 2016 (5 pages).
Chinese-language Office Action issued in counterpart Chinese Application No. 201680003589.8 dated Sep. 13, 2018 with English translation (22 pages).

* cited by examiner

METHOD AND DEVICE FOR TESTING GEARWHEELS

CROSS REFERENCE TO RELATED APPLICATIONS

This application is a continuation of PCT International Application No. PCT/EP2016/050668, filed Jan. 14, 2016, which claims priority under 35 U.S.C. § 119 from German Patent Application No. 10 2015 204 554.4, filed Mar. 13, 2015, the entire disclosures of which are herein expressly incorporated by reference.

BACKGROUND AND SUMMARY OF THE INVENTION

The invention relates to a method and to an apparatus for testing gearwheels with at least one optical test method. Optical test methods and apparatuses for carrying out the latter are known from the prior art, in particular DE 10 2009 023 722 A1.

The invention is described below in conjunction with bevel gearwheels and hypoid gearwheels for mass-produced axle drives of motor vehicles, but the invention is not limited to such gearwheels.

The gearwheels for axle drives of this type are tested prior to their use with respect to geometrical deviations, for example concentricity, and with respect to further parameters, for example the position and size of the contact pattern, on what are referred to as running test machines. The intention is therefore for the running and noise behavior of the gearwheels in engagement with each other to be assessed prior to the actual use thereof.

In addition to the parameters mentioned, the running and noise behavior is also dependent on further influencing factors. These influencing factors include, for example, material deposits or abrasions on the tooth flanks, surface damage in general, and the type and manner of the precise machining of the tooth flanks, what is referred to as micro geometry of the tooth flanks.

Previous optical test methods are generally based on a color application method in which a test color is applied to at least one of the gearwheels and here, in particular, to the tooth flanks. The two gearwheels are then brought into engagement with each other on the running test machine and subjected to a test torque. By rolling the gearwheels, the color application in the regions in which the gearwheels are in contact for transmitting movement, is abraded. As soon as a stationary state of the color abrasion has arisen, individual image data of the tooth flank are captured with a camera system when the gearwheels are at a standstill. By means of a corresponding evaluation of the image data, the contact pattern position and size can be assessed in an automated manner.

It is an object of the invention to provide an improved test method for gearwheel pairs, in particular with crossed spindles, and to provide an apparatus on which said method can be carried out.

This and other objects are achieved by an apparatus and a method in accordance with embodiments of the invention.

According to the invention, at least one of two different optical test methods is carried out for assessing the running and noise behavior of the gearwheel pair. This optical test method, or at least the capturing of image data, is carried out here while a gearwheel to be tested is rotated at a test speed. A gearwheel within the context of the invention should be understood as meaning, in particular, gearwheels for the form-fitting transmission of movement and power, preferably cylindrical gears, bevel or hypoid gears, worm or helical gears and crown gears.

In order to permit a particularly precise capturing of image data, at least one position sensor is provided which captures the rotational position of the gearwheel to be tested. As soon as the latter is in a test position, a camera is activated in such a manner that the camera captures image data of a tooth flank of the gearwheel and supplies the image data for further processing by one of the optical test methods.

Furthermore, the first optical test method is provided in particular to assess damage to the tooth flank to be tested, in particular the surface thereof. The second optical test method is provided in particular to assess the design of a contact pattern, or the size and position of a contact surface between the gearwheel to be tested and a further gearwheel which can be brought into engagement with said gearwheel. It has proven advantageous here, prior to carrying out the second optical test method, to apply a test medium layer, in particular a contact pattern paint, to those regions of the gearwheel which are to be tested.

Furthermore advantageously, it is provided that one of the optical test methods can be carried out at least partially isochronously with a further test method which is based in particular on the measurement of a gearwheel geometry. In particular, a further test method of this type should be understood as meaning a concentricity test, a single-flank rolling test or other, in particular standard, gearwheel measurement procedures.

Owing to the fact that the test medium layer is applied prior to the second optical test method and preferably between the two optical test methods, the micro geometry, i.e. in particular the surface condition of at least one of the tooth flanks, can be assessed particularly readily with the first test method, while in particular the contact pattern position and size can be particularly readily assessed with the second test method. Furthermore preferably, a plurality of first test methods and/or a plurality of second test methods are carried out.

Within the context of the invention, a test apparatus for carrying out an optical test method can be combined with a gearwheel testing machine, in particular with crossed or parallel spindles, or can be integrated in the gearwheel testing machine. A test apparatus of this type is preferably provided for testing at least one gearwheel pair and, for this purpose, can drive the latter at a predefinable speed and load the latter with a predefinable torque. Furthermore preferably, the test apparatus is designed for recording measurement values, in particular for carrying out a concentricity test and a single-flank rolling test. Furthermore preferably, the test apparatus is designed as a running test machine, in particular for bevel gears or hypoid gears, or a test machine for testing cylindrical gears.

Within the context of the invention, the test position should be understood as meaning that position of the gearwheel to be tested in which image data of that region of the gearwheel which is provided for checking can be recorded by one of the cameras. The test position should preferably be understood as meaning a certain rotational path which the gearwheel to be tested brushes over during the exposure duration of the camera which captures the image data.

Within the context of the invention, a tooth flank should be understood as meaning that region of a gearwheel which can be directly contacted by a further gearwheel in order to transmit movement to said further gearwheel. Within the context of the invention, a first type of tooth flanks should be understood as meaning a first group of tooth flanks of a gearwheel, which tooth flanks are at least similar or identical in respect of their geometrical properties. Preferably, a first type of tooth flanks should be understood as meaning all leading flanks, and a second type of tooth flanks should be understood as meaning all trailing flanks of a gearwheel. Furthermore preferably, a first type of tooth flank should be understood as meaning the thrust or traction flanks, and a second type of tooth flank should be understood as meaning the traction or thrust flanks, and therefore in particular all tooth flanks of a gearwheel are covered by these two types of tooth flanks.

Within the context of the invention, the capturing of image data should be understood as meaning the capturing of an, in particular optical, image of at least one tooth flank or of one type of tooth flanks. Furthermore preferably, the captured image data should be understood as meaning a photo of at least one tooth flank of the gearwheel to be tested, and preferably at least one color image of such a tooth flank, furthermore preferably of a plurality of tooth flanks and particularly preferentially of all of the tooth flanks.

Furthermore preferably, the image data are captured in such a manner that they can be indirectly or directly stored on a data processing system and can be processed by the latter, and in particular are present in the form of at least one digital image. The capturing of image data should therefore preferably be understood as meaning the recording of a digital image, preferably a digital color image.

Within the context of the invention, a first test method should be understood as meaning a method based on the captured image data, wherein, for the first test method, the image data are captured prior to the application of the test medium layer to the tooth flanks.

Furthermore, within the context of the invention, a second test method should be understood as meaning a method based on the captured image data, wherein, for the second test method, the image data takes place after the test medium layer is applied to the tooth flanks. Furthermore preferably, a plurality of first and/or a plurality of second test methods can be carried out.

The test apparatus according to the invention can preferably be integrated as a camera-based test system in the running test machine. The test apparatus preferably has at least one, but preferably two, cameras, in particular digital cameras. The cameras are arranged in one or more protective housings with preferably at least one protective flap. Furthermore preferably, the camera-based test system has an illuminating device. The protective housing here is designed in such a manner that the cameras are protected from soiling and external mechanical influences. Furthermore, the illumination is designed in such a manner that at least one tooth flank whose image data is to be captured can be illuminated with said illumination. The illuminating device preferably has an illuminating housing for protection against external influences. The illuminating device is preferably arranged with at least one of the cameras in the protective housing. The illuminating device is preferably designed as a stroboscopic light source. It should preferably be understood by this that the illuminating device every so often emits light beams for illuminating the tooth flank which is provided for capturing image data (first operating mode) and every so often does not emit any light beams for this illumination (second operating mode).

The test apparatus preferably has a plurality of illuminating devices, preferably the number of the illuminating devices corresponds to the number of cameras which are provided for capturing image data. Preferably, one light source can be provided for a plurality of illuminating devices, preferentially each illuminating device has a dedicated light source. Furthermore preferably, the number of illuminating devices is lower than the number of cameras. One is preferable, two are preferential and three or a multiplicity of illuminating devices are particularly preferential.

It has been shown that, in particular on the basis of the surface condition of gearwheels, a certain illuminating strength of the illuminating device contributes to a particularly advantageous capturing of image data. The illuminating strength of the illuminating device is preferably selected from a certain range, the latter is preferably greater than 200 000 lux, furthermore preferably greater than 400 000 lux, preferentially greater than 550 000 lux, and furthermore preferably smaller than 1 200 000 lux, preferably smaller than 750 000 lux and preferentially smaller than 650 000 lux and very particularly preferentially the illuminating strength is at least substantially 610 000 lux. Furthermore preferably, the illuminating strength of at least two illuminating devices is identical in magnitude and preferentially the illuminating strength of all illuminating devices are identical. Furthermore preferably, the illuminating strength of the illuminating device can be controlled, preferably can be dimmed.

It has furthermore been determined that the capturing of image data can be influenced in an advantageous manner if the illuminating device that is provided for capturing image data is arranged at a certain distance range from that region of the gearwheel to be tested. The distance of the illuminating device from said region is preferably greater than 10 mm, is furthermore preferably greater than 25 mm, is preferentially greater than 50 mm and is particularly preferentially greater than 125 mm, and is furthermore preferably smaller than 750 mm, preferably smaller than 500 mm, preferentially smaller than 300 mm and particularly preferentially smaller than 250 mm and is very particularly preferentially at least substantially 200 mm. Furthermore preferably, it has been determined that the combination of illuminating strength and distance of the illuminating device have a particularly advantageous effect on the captured image data.

Furthermore, the optical test system is designed in such a manner that, with one of the cameras, the image data of the tooth flanks of the thrust side (thrust flank) of the gearwheel to be tested can be captured and, with the other camera, the tooth flanks of the traction side (traction flank) of the gearwheel to be tested can be captured. In particular by means of this division of the cameras, particularly efficient testing of the gearwheels is made possible.

The image data are preferably captured with a certain exposure duration or exposure time which is selected from a range depicted below. Within the context of the invention, the exposure duration/time should be understood as meaning the period of time in which a photo sensitive medium (for example CMOS or CCD sensor) is exposed to the light for recording an image, i.e. for capturing the image data. It has been shown that, in the case of short exposure durations, the quality of the captured image data is inadequate, in particular because known optical cameras cannot capture the image data rapidly enough. Furthermore, it has been shown that a long exposure duration likewise leads to inadequate quality of the captured image data. Investigations have shown that an exposure duration is selected from a range which is preferably greater than 2 μs (micro seconds), is furthermore preferably greater than 25 μs and is preferentially greater than 70 μs, and is furthermore smaller than preferably 500 μs, is furthermore preferably smaller than 250 μs, is preferentially smaller than 120 µs and very particularly preferentially the exposure time is at least substantially 100 µs. In particular in the case of an exposure duration of this type, it is made possible to capture image data of adequate quality within a short time. It is preferably provided that the two cameras operate with an exposure duration from this range for the exposure duration, and preferably the cameras operate with the same exposure duration.

In order to record qualitatively sufficiently good images of the tooth flanks, it is preferably provided to activate at least one of the cameras, preferably the two cameras, by way of the at least one position sensor, or to trigger the capturing of image data by way of the position sensor. The activating should be understood here as meaning in particular that the camera captures image data from the region of the gearwheel to be tested. The position sensor is therefore designed to capture the rotational position of at least one of the gearwheels, preferably of the gearwheel to be tested. The capturing of the rotational position can take place directly on one of the gearwheels or indirectly on a shaft which is connected directly or via a transmission ratio to one of the gearwheels. Furthermore preferably, the illuminating device is likewise activated on the basis of the captured rotational position. The illuminating device preferably emits light beams for illuminating the region provided for capturing image data depending on a rotational frequency of the gearwheel to be tested, or the test speed. The activation of the exposure device can preferably take place indirectly via one of the cameras.

For example, during a first test run in which, for example, concentricity testing is carried out, the tooth flanks are recorded (capturing of image data) by a camera system (first and/or second camera and at least one illuminating device) without application of a test medium layer, i.e. without application of a contact pattern paint. By means of image data of this type, the surface condition of the tooth flanks can then be particularly readily assessed. The image data serve, in particular, for testing whether there is damage to the tooth flank surface, for example for assessing whether the tooth flanks are splayed. Such "errors" of the tooth flanks can be identified in particular with one of the first optical test methods.

Preferably, after the first optical test method has been carried out or after the image data for the test method have been captured, a test medium layer can be applied to the gearwheel to be tested, in particular in order to capture image data for one of the second optical test methods.

Furthermore preferably, it is also made possible for the image data for the second optical test method to be captured without image data for one of the first optical test methods having been captured beforehand.

After the color application, i.e. in particular the application of the test medium layer, the contact patterns of the gearwheel to be tested are captured, for example, during the single-flank rolling test. The image data serve for detecting and evaluating the contact pattern or for testing whether seizures are present. In particular, the efficiency can be increased further by such a test sequence.

By means of the proposed method, the tooth flanks can be tested both for damage and splayed tooth flanks and also, in particular by application of a test medium layer to the gearwheel to be tested, can be tested in respect of the formation of the contact pattern. According to the invention, this is made possible without retooling and furthermore preferably without a resultantly caused interruption of the test sequence.

According to the invention, the protective housing protects the test apparatus and, in particular, the cameras and furthermore preferably also the illuminating device. The test apparatus is preferably protected in such a manner that no test medium passes onto the cameras and preferably also onto the illuminating device. In particular by means of the protective housing, particularly high freedom of the apparatus from maintenance can be achieved and therefore the efficiency of the test system can be increased.

The image data are preferably captured in the form of color images. It has been shown that particularly good error recognition on the tooth flank surface can be achieved with color images.

The evaluation and processing of the image data produced is carried out automatically in the various test methods, in particular the first and second test method, according to preferably different algorithms.

Preferably, for the recognition of errors, in particular around damage in the region of a tooth tip and preferably around errors to the tip edges of the gearwheel to be tested, the first test method set forth below is carried out:

1. a filter is used to emphasize object details, preferably to emphasize the tip edge (unsharp masking),
2. the image data are transformed into a gray value image,
3. the color values and gray values are inverted,
4. noises are reduced by media filtering and therefore the damaged area is emphasized,
5. a binary image is produced by the segmentation method with an adaptive threshold value method,
6. the binary image is reduced to the corresponding region of the tooth flank to be investigated, in particular the region of the tip edge, and
7. filtering is carried out once again in order only still to depict possible damaged areas on the image,
8. therefore the damaged areas in the investigated region of the tooth flank can be identified.

An error area for an individual tooth flank, for a plurality of individual tooth flanks or for all of the tooth flanks can be calculated from the recorded image data. An error area arises here in particular in a deviation of a color value or gray value from a predefinable average value.

It is therefore possible to calculate preferably an accumulated, or preferentially an individual, error area and, when threshold values for an individual error or for the entire error area are exceeded, the threshold values are interpreted as damage in the investigated tooth flank region. Threshold values of this type preferably describe a relative area with respect to the entire area of a tooth flank, or an absolute area size. With a differentiated method, the severity of the error can also be assessed depending on the error area.

A test method is described below which is suitable for error recognition on tooth flanks which are not completely splayed, i.e. for recognizing surface damage on the tooth flank to be tested. Such a test method can be used as a first test method.

This test method is based here on the fact that splayed tooth flanks are distinguished by a lighter and light-reflecting surface; the said surfaces can be recognized by a corresponding test method. For the recognition of such errors, it is proposed that:

1. a filter is used to emphasize object details of the tooth flank (unsharp masking),
2. the image is transformed into a gray value image,
3. holes (a region with dark pixels surrounded by lighter pixels) are filled,
4. noises are reduced by media filtering, 5. a binary image is produced by the segmentation method with an adaptive threshold value method, 6. the binary image is reduced to the corresponding region to be investigated (tooth flank in this case), 7. small freak values of the area found are filtered out, and 8. thus the area of the lapped region is identified.

In a further method step, the image data processed in this manner can be compared with a desired range for fine processing, in particular of the desired lapped region. This comparison can take place in particular in the form of a differentiation formation or formation of a proportional number. The comparison result can finally be compared with a threshold value, and if the threshold value is reached or fallen short of, then the tooth flank is defined as not being splayed.

Further errors of the tooth flanks can also be assessed with the recorded image data. What are referred to as seizures involve, within the context of the invention, spot impressions by means of material deposits and material abrasions or fractures on the surface of the tooth flanks. In order to detect these, a further optical test method is proposed which is likewise based on image data which are captured preferably before or preferentially after the application of the test medium layer, in particular the contact pattern paint. For this test method, it is proposed that:

1. a filter is used to emphasize object details of the tooth flank (unsharp masking), 2. the image is transformed into a gray value image, 3. noises are reduced by media filtering, 4. a binary image is produced by the segmentation method with an adaptive threshold value method, 5. the binary image is reduced to the corresponding region to be investigated (tooth flank in this case), 6. small freak values are filtered out, and 7. thus the damaged area is determined.

If the damaged area determined with this test method is greater than a predefinable threshold value, the damaged area can be identified as a seizure on the tooth flank.

Previous optical test methods for evaluating the contact pattern, such as those proposed, for example, in DE 10 2009 023 722 A1, are based on producing a gray value image from the recorded color image image data and generating a binary image by a known segmentation method with a global threshold value method. The binary image can be used for evaluating and assessing the contact pattern.

For the second optical test method, i.e. the test method which is used after a test medium layer has been applied to the tooth flanks, the use of a segmentation method with an active contour of the tooth flanks is proposed, in particular in order to obtain a higher quality of binary image of the contact pattern. In the second optical test method, the object contour is described in particular by a curve determined in an optimization method or by a predefinable parametric curve and, therefore, the area of the contact pattern can be defined more precisely.

The actual image produced in this manner is then preferably compared with desired criteria, for example a minimum contact pattern size, a certain gravitation position of the contact pattern or further geometric minimum or maximum extents. In particular by means of comparisons of this type, a conclusion can be drawn regarding possible errors of the contact pattern.

In a preferred embodiment, the test apparatus can be used on a device for testing cylindrical gears (pinion/gear). A device of this type has axially parallel shafts for accommodating a cylindrical gear pair. Preferably, at least one camera and at least one illuminating device for capturing image data for at least one of the optical test methods are aligned with a type of the tooth flanks, for example trailing flank pinion, leading flank pinion, trailing flank gear, leading flank gear, of a cylindrical gear to be tested. Preferably, the plurality of cameras and, furthermore preferably, a plurality of illuminating devices are arranged on the device, and preferentially at least one camera and at least one illuminating device for each type of tooth flank to be tested are arranged on the device. For testing cylindrical gears, two cameras and two illuminating devices are preferably arranged on this device.

Other objects, advantages and novel features of the present invention will become apparent from the following detailed description of one or more preferred embodiments when considered in conjunction with the accompanying drawings.

DETAILED DESCRIPTION OF THE DRAWINGS

Figure 1:
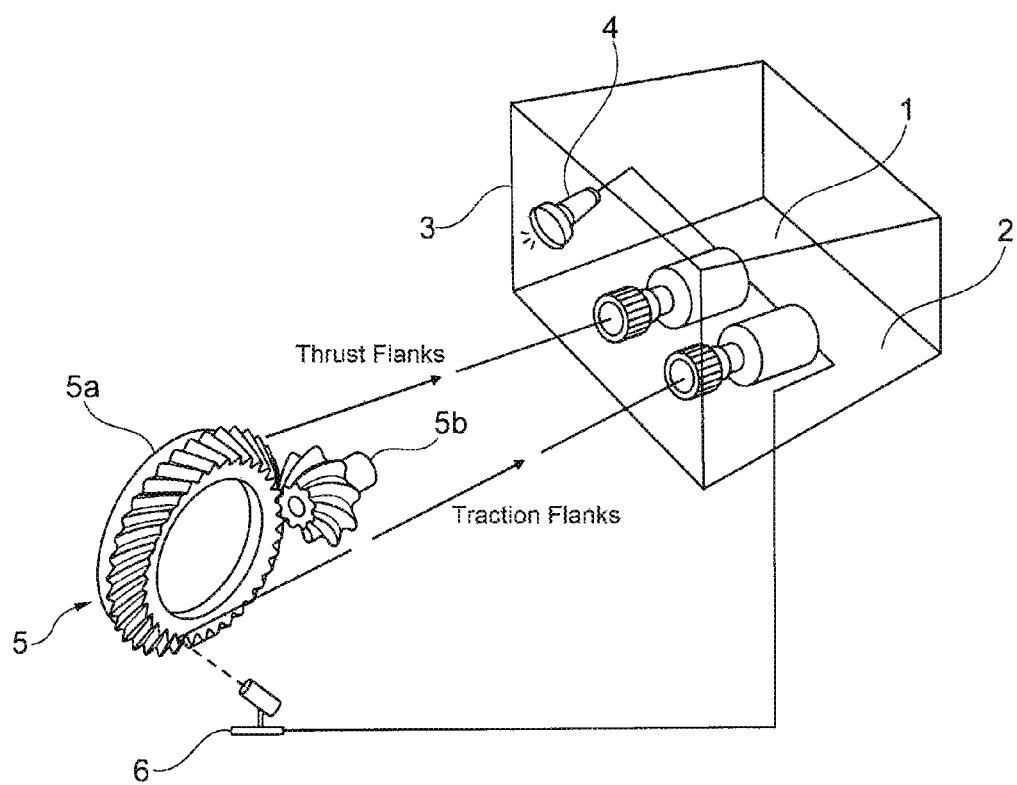
FIG. 1 is a schematic perspective view of the test device.

In FIG. 1, the gearwheel pair 5 to be tested is illustrated as a ring gear 5a which can be contacted by the bevel pinion 5b. The tooth flanks of the ring gear 5a are tested with the running test machine (not illustrated); for this purpose, the latter has a crossed spindle. In order to capture the image data of the tooth flanks, a first camera 1 and a second camera 2 are arranged in a protective housing 3. The illuminating device 4 is also arranged in the protective housing 3.

The first camera 1 is oriented for capturing the image data from the thrust side of the tooth flanks. The second camera 2 is oriented for capturing the image data from the traction side of the tooth flanks.

Furthermore, the test apparatus has at least one contactless position sensor 6 for capturing the rotational position of the ring gear 5a. The capturing of image data is controlled by way of the rotational position, which is captured by the position sensor 6, in such a manner that image data of the different tooth flanks are captured when the tooth flanks are in the same position in each case. The image data captured by the cameras 1, 2 are transmitted to an electronic data processing system (not illustrated). Furthermore, the test method according to the invention can be carried out on the data processing system.

Figure 2:
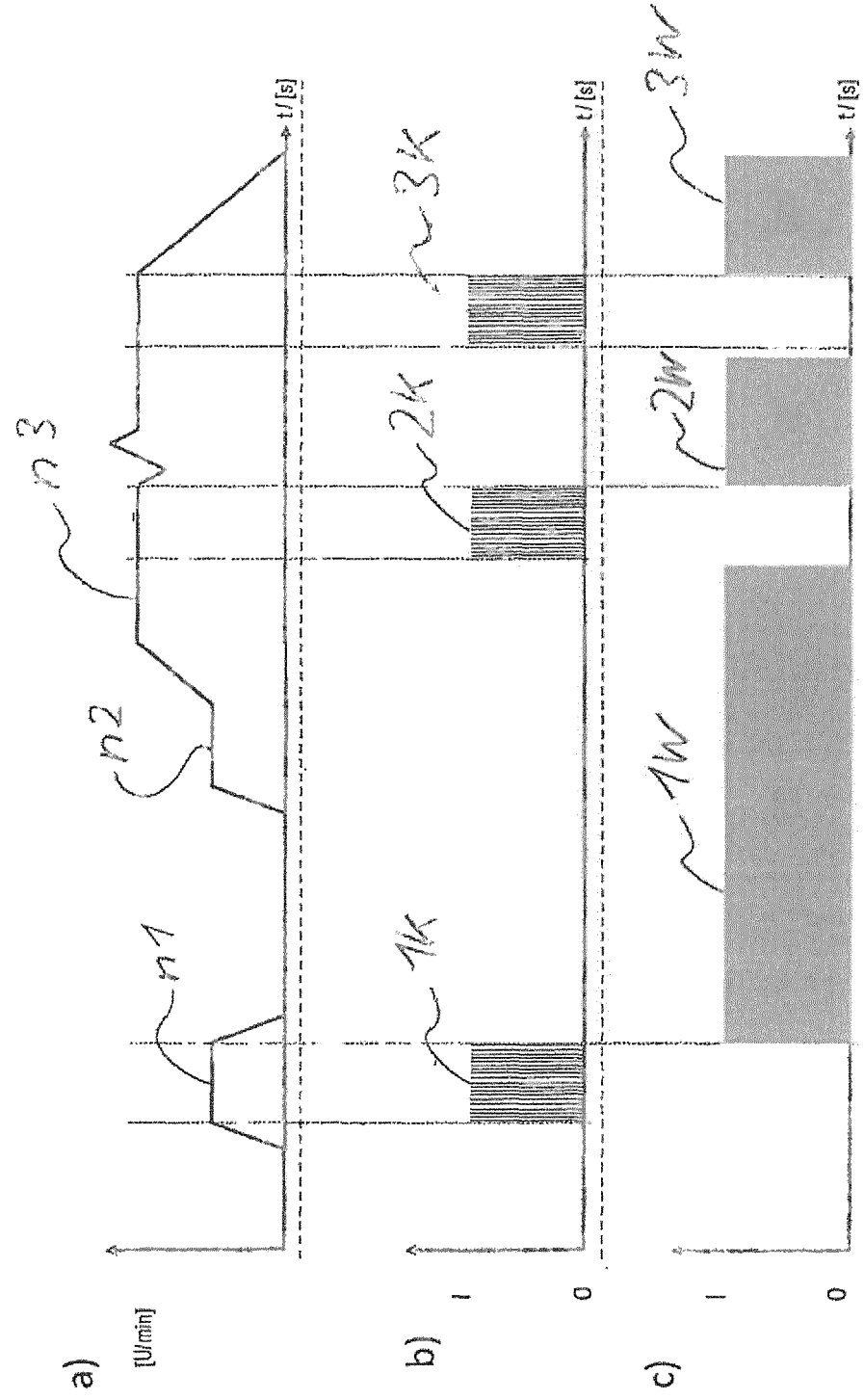
FIG. 2 is a graph showing an exemplary method sequence.

FIG. 2 is an exemplary illustration of the sequence of a test method according to the invention. Here, subsection (a) of FIG. 2 illustrates the speed of the running test machine over time, subsection (b) illustrates the activity of the cameras over time, and subsection (c) illustrates the evaluation activity of the data processing system over time.

First of all, the gearwheel pair to be tested is accommodated and aligned on the running test machine. Then, for example, the concentricity of the gearwheel pair is tested. For this purpose, the gearwheel pair is driven at a first test speed n1. The tooth flanks are preferably metallically blank here. Furthermore, image data of the traction flanks and the thrust flanks are captured with the first and the second camera, 1K. The image data are supplied to at least one first test method since, in particular, errors which relate to the precise geometry/surface condition of the tooth flanks can be particularly readily recognized therewith.

In particular, the captured image data are evaluated, preferably directly, after the capturing, 1W. It is therefore made possible that, if the identified errors on the tooth flanks exceed a threshold value, the test sequence is ended at this point. Furthermore, it is also made possible for only some of the captured image data to be evaluated or for the latter not yet to be evaluated at this time.

After continuation of the test method, first of all the test medium layer is applied to the tooth flanks. This preferably takes place at a relative low speed n2, preferably said speed is lower than the test speed n1 in order thereby to permit, in particular, a uniform application of the layer.

Over the further course of the test method, the contact patterns of the traction flanks 2K and also of the thrust flanks 3K are investigated successively by capture of image data and carrying out of one of the second optical test methods. For this purpose, the gearwheel pair is driven at the test speed n3 and subjected to test torque. The capturing and evaluating of image data 2W, 2K, 3W, 3K can be carried out at the same time with further test methods, for example with a single-flank rolling test.

The test method according to the invention can therefore be integrated into the "normal" test sequence and, despite an improvement in the assessment of the gearwheels there is virtually no disadvantage in terms of time.

The test sequence illustrated here is exemplary. By means of the apparatus according to the invention and the method according to the invention, it is made possible to carry out the optical test methods individually and independently or in combination with one another; it is preferential here that first of all one of the first optical test methods without application of a test medium layer is carried out and, after said test method, a second optical test method with application of the test medium layer is carried out.

Figure 3:
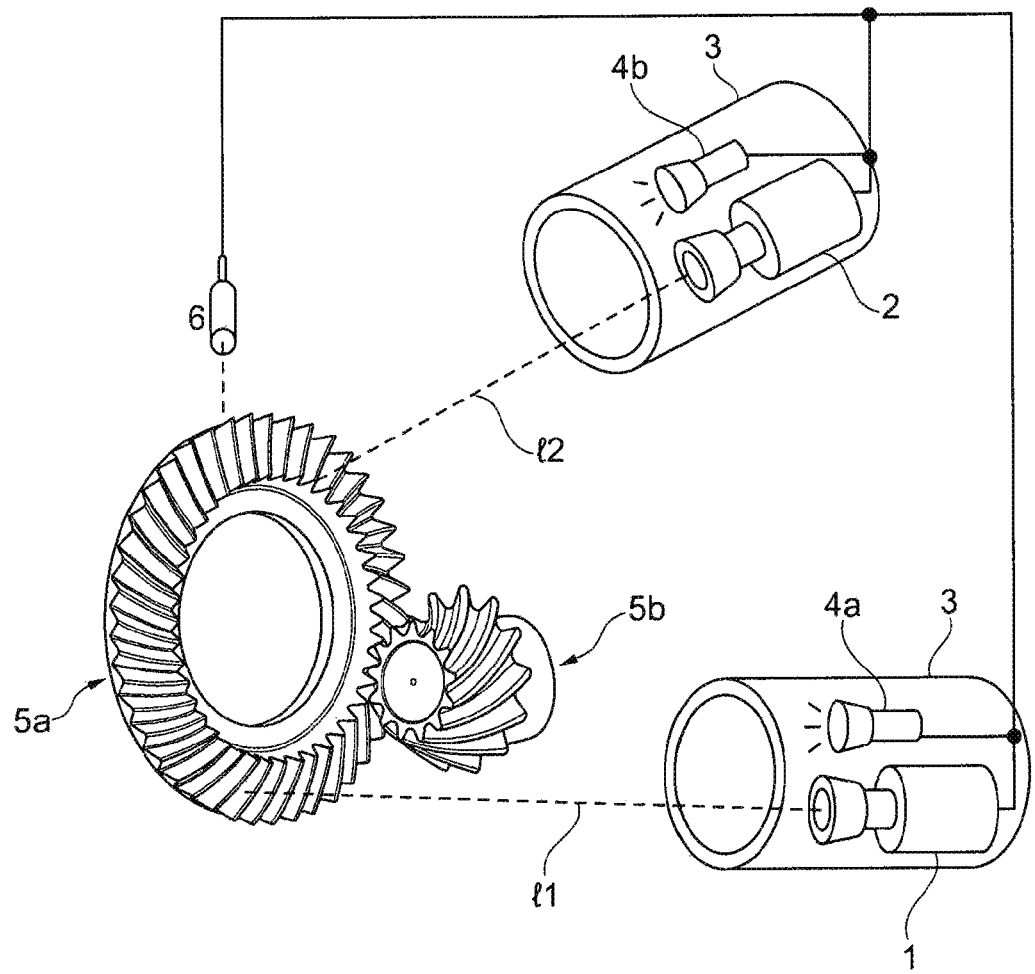
FIG. 3 is a schematic perspective view of a further test device.

FIG. 3 shows a further embodiment of an apparatus according to the invention for testing gearwheels. The apparatus has a first camera 1 with an illuminating device 4a and a second camera 2 with a further illuminating device 4b. The first illuminating device 4a is arranged at a first illuminating distance l1 for illuminating a first type of tooth flanks, and the second illuminating device is arranged at an illuminating distance l2 for illuminating a second type of tooth flanks. The first camera 1 is therefore designed for capturing the image data of the tooth flanks of the traction side of the gear wheel 5a to be tested, and the second camera 2 is designed for capturing the image data of the second type of the tooth flanks of the thrust side. The position sensor 6 contactlessly captures the rotational position of the gearwheel 5a to be tested and activates one of the cameras 1, 2 and the illuminating device 4a, 4b, which is assigned to said cameras, when that region of the gearwheel 5a which is provided for capturing image data, i.e. the tooth flank to be tested, is in a test position.

If the test position is recognized by the position sensor 6, the illuminating device is set into its first operating state, and the tooth flanks are illuminated such that image data can be captured by the associated camera. After the image data are captured, the illuminating device is set again into its second operating state.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A test apparatus for carrying out an optical test method for a gearwheel, comprising:
    a first camera that captures image data of a first type of tooth flanks of the gearwheel to be tested;
    a position sensor that determines a rotational position of the gearwheel to be tested;
    a control device that evaluates the rotational position determined by said position sensor and that activates the first camera based on said rotational position; and
    a first illuminating device configured to illuminate a region of the gearwheel to be tested, which region is provided for capturing image data.

2. The apparatus as claimed in claim 1, further comprising:
    a second camera that captures image data of a second type of tooth flanks; and
    a second illuminating device configured to illuminate a further region of the gearwheel to be tested, in that said further region for capturing image data is provided with the second camera.

3. The apparatus as claimed in claim 2, wherein
    at least one of the illuminating devices has an illuminating strength from a range that is greater than 200 000 lux and less than 1 000 000 lux.

4. The apparatus as claimed in claim 3, wherein the range is greater than 550 000 lux and less than 650 000 lux.

5. The apparatus as claimed in claim 3, wherein
    at least one of the illuminating devices is arranged at an illuminating distance from the region on the gearwheel to be tested, for the illumination of which said illuminating distance is from a range which is greater than 10 mm and less than 750 mm.

6. The apparatus as claimed in claim 5, wherein the range is greater than 125 mm and less than 250 mm.

7. The apparatus as claimed in claim 1, wherein the position sensor operates according to a contactless measurement method.

8. The apparatus as claimed in claim 2, wherein at least one of said first and second cameras has an exposure time which is selected from a range which is greater than 2 μs and less than 250 μs.

9. The apparatus as claim in claim 8, wherein the range is greater than 70 μs and less than 120 μs.

10. The apparatus as claimed in claim 2, wherein at least one of the first and second cameras is protected from the gearwheels with a protection device at least partially arranged between the gearwheels and the camera or the cameras.

11. The apparatus as claimed in claim 1, wherein
    the gearwheels are accommodate on two spindles arranged perpendicularly to each other, and
    the apparatus is designed for testing bevel gearwheels or hypoid gearwheels.

12. A method for testing at least one gearwheel with a test apparatus designed for subjecting the gearwheels to a predeterminable test torque and for driving the gearwheels at a predeterminable test speed, the test apparatus having a camera-based test device for carrying out an optical test method in which image data can be captured and evaluated, the method comprising the steps of:
    providing a gearwheel pair with two gearwheels;
    accommodating the gearwheels on the test apparatus;
    driving the gearwheels at a test speed;
    recording a rotational position of the gearwheel to be tested by way of a position sensor;

evaluating said rotational position and activating at least one camera for capturing image data when the gearwheel to be tested is in a test rotational position; and processing the captured image data with a first or second optical test method.

13. The method as claimed in claim 12, wherein an illuminating device has a first and a second operating state, and in the first operating state, the illuminating device emits light radiation for illuminating a region of the gearwheel to be tested, which region is provided for capturing image data, in the second operating state, the illuminating device does not emit any such light radiation, the illuminating device is set directly into the first operating state before image data from said region are captured, and the illuminating device is set directly into the second operating state after the image data from said region are captured.

14. The method as claimed in claim 13, wherein before the second optical test method is carried out, a test medium layer is applied to at least a first type of the tooth flanks, after this application, the gearwheel pair is driven at one test speed, and in the process, the applied test medium layer is changed by contact of the gearwheels with each other, and after or during said change, the camera for capturing image data is activated.

15. The method as claim in claim 14, wherein the testing medium layer is a contact pattern paint, and the applied test medium layer is changed by being abraded.

16. The method as claimed in claim 14, wherein the test medium layer is applied to tooth flanks of both types of tooth flanks of the gearwheel to be tested.

17. The method according to claim 16, wherein the test medium layer is applied to all tooth flanks of said gearwheel.

18. The method as claimed in claim 9, wherein the gearwheels for the first test method are driven at the first test speed and in a first phase are subjected to a first positive test torque, and image data of at least one leading flank of the gearwheel to be tested or of the two gearwheels are captured.

19. The method as claimed in claim 18, wherein during a second phase, the gearwheels are subjected to a second test torque which is directed counter to the first test torque, and during the second phase, image data of at least one trailing flank of the gearwheel to be tested or of the two gearwheels are captured.

20. The method as claimed in claim 12, wherein the gearwheels for the second test method are driven at the second test speed and in a first phase are subjected to a positive test torque which leads to an at least partial abrasion of the test medium layer on the first type of tooth flanks, in that image data of said type of tooth flanks are captured for evaluation when a virtually stationary state of the test medium layer has arisen, and in a second phase of said test method, the gearwheels are subjected to a negative test torque which leads to an at least partial abrasion of the test medium layer on the second type of tooth flanks, further image data of said type of tooth flanks are captured for evaluation when a virtually stationary state of said test medium layer has arisen.

* * * * *